(12) United States Patent
Wu et al.

(10) Patent No.: US 11,583,502 B2
(45) Date of Patent: Feb. 21, 2023

(54) PHARMACEUTICAL COMPOSITIONS COMPRISING A THYROID HORMONE BETA AGONIST, METHOD OF USE AND METHOD MAKING THEREOF

(71) Applicant: GANNEX PHARMA CO., LTD., Shanghai (CN)

(72) Inventors: Jinzi Jason Wu, Shanghai (CN); Xuyu Chai, Shanghai (CN)

(73) Assignee: GANNEX PHARMA CO., LTD., Shanghai (CN)

( * ) Notice: Subject to any disclaimer, the term of this patent is extended or adjusted under 35 U.S.C. 154(b) by 1 day.

(21) Appl. No.: 17/301,870

(22) Filed: Apr. 16, 2021

(65) Prior Publication Data

US 2021/0259977 A1 Aug. 26, 2021

(30) Foreign Application Priority Data

Feb. 20, 2020 (CN) .......................... 202010105909.9
Feb. 20, 2021 (CN) .......................... 202110194256.0

(51) Int. Cl.
*A61K 9/48* (2006.01)
*A61K 31/661* (2006.01)
*A61K 9/14* (2006.01)

(52) U.S. Cl.
CPC ............ *A61K 9/4825* (2013.01); *A61K 9/146* (2013.01); *A61K 9/4833* (2013.01); *A61K 9/4858* (2013.01); *A61K 9/4866* (2013.01); *A61K 9/4875* (2013.01); *A61K 31/661* (2013.01)

(58) Field of Classification Search
CPC .... A61K 9/4825; A61K 9/146; A61K 9/4833; A61K 9/4858; A61K 9/4866; A61K 9/4875; A61K 31/661
See application file for complete search history.

*Primary Examiner* — Robert A Wax
*Assistant Examiner* — Olga V. Tcherkasskaya
(74) *Attorney, Agent, or Firm* — Michael Ye, Esq.; Rimon Law

(57) ABSTRACT

A pharmaceutical formulation contains the following components in part by weight: (a) 1 part of the compound represented by Formula (I),

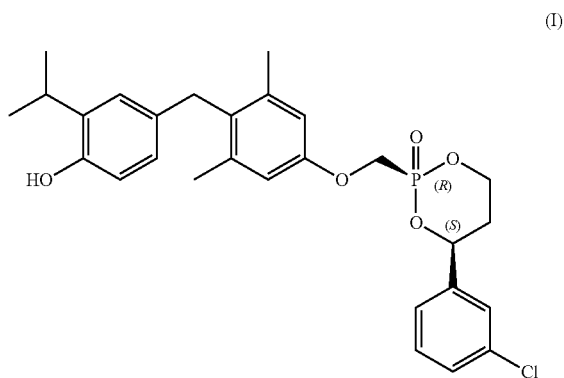

(b) 16 to 600 parts of a meltable and dispersible carrier comprising poloxamer and polyethylene glycol in a poloxamer-to-polyethylene glycol weight ratio of 1-0.5 to 1:27, and (c) 0.2 to 100 parts of a non-volatile weak acid. The pharmaceutical formulation helps to improve the in vitro dissolution of the compound of Formula (I).

19 Claims, 2 Drawing Sheets

PHARMACEUTICAL COMPOSITIONS COMPRISING A THYROID HORMONE BETA AGONIST, METHOD OF USE AND METHOD MAKING THEREOF

RELATED APPLICATIONS

This application claims priority of Chinese Patent Application No. 202010105909.9, filed on Feb. 20, 2020 and Chinese Patent Application No. 202110194256.0, filed on Feb. 20, 2021. The entirety of the aforementioned application is incorporated herein by reference.

FIELD

The present application generally relates to pharmaceutical preparations, and specifically relates to a pharmaceutical compositions comprising a thyroid hormone beta (THR-β) agonist.

BACKGROUND

Steatohepatitis is a chronic inflammatory disease, thus long term medication is preferred. In order to be efficacious in treating steatohepatitis, the dissolution of the drug in the gastrointestinal tract is a prerequisite for transmembrane transport and absorption into the human body.

The compound shown Formula (I) (molecular formula is $C_{28}H_{32}ClO_5P$, molecular weight is 514.98, CAS registration number is 852948-13-1) is a new oral thyroid hormone beta agonist (THR-β agonist). This compound effectively promotes the decomposition of fatty acids and stimulates the biogenesis of mitochondria by selectively activating THR-β and regulating the expression of downstream genes such as CYP7A and SREBP-1c, thus reducing low-density lipoprotein and triglyceride levels, which in turn reduces lipotoxicity and improves liver function and reduces liver fat. The compound of Formula (I) is a highly effective and low toxic candidate drug for nonalcoholic steatohepatitis (NASH). Formula (I) is shown as follows:

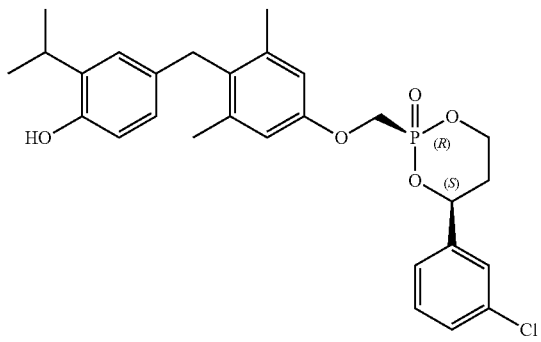

The compound of Formula (I), however, is a lipophilic drug that is highly insoluble in water. Its solubility in hydrochloric acid solution, buffer, and water without surfactant at 37° C. and pH 1.0~9.0 is less than 0.5 ng/ml. The very low solubility limits its use in research and development as a drug candidate.

For drugs with poor solubility, in vitro dissolution evaluation is a simple and effective method for predicting and comparing dissolution in vivo. In vitro dissolution evaluation is also an important criterion for screening prescription drugs for quality control. The solubility of the compound of Formula (I) in a medium containing no surfactant is less than 0.5 ng/ml. Therefore, in order to completely dissolve the compound in a conventional 900 ml medium for a 10 mg/unit dose formulation, it is necessary to increase the solubility of the compound to at least 11.11 μg/ml. It would be difficult to achieve such a target with conventional solubilization technology.

For example, the relatively low melting point (65° C.~95° C., depending on the crystal type) and low thermostability (when heated at 80° C. for 3.5 hours, 10.2% of the drug will undergo highly undesirable degradation reactions) of the compound of Formula (I) limit the application of the hot-melt method of solubilization; especially those hot-melt methods that prepare solid dispersions at a glass transition temperature (Tg value) greater than 100° C.

A commonly used solubilization method is the solvent method. Drugs that are poorly soluble in water are usually first dissolved in an organic solvent with good solubility such as methanol, acetone, dichloromethane, etc. Suitable polymer carrier materials are then added to the organic solvent to allow the drug fully dissolved or dispersed in the solution. The organic solvent is then removed (e.g. by solvent volatilization or spray drying) to produce a solid dispersion in which the drug is uniformly dispersed in the carrier material. While this method is suitable for the preparation of thermally unstable solid dispersions, but has significant defects: (1) it needs to be produced in a strictly controlled explosion-proof workshop; (2) the use of large amount of organic solvents, (3) the removal of organic solvents is slow (requires repeated oven drying-vacuum oven drying to remove); and (4) the toxicity of residual organic solvent to human body.

In addition, the compound of Formula (I) is prone to form a solvate; so the solvent method also has the defect that the compound of Formula (I) is converted into a solvate during the preparation of the solid dispersion.

Therefore, the technical problem to be solved by the present invention is to provide a pharmaceutical composition comprising the compound of Formula (I) and a preparation method thereof, that will maximize the dissolution of the compound of Formula (I) without the many defects of conventional solubilization methods.

SUMMARY

One aspect of the present application relates to a pharmaceutical composition that comprises, in parts by weight,
(a) 1 part of a compound of Formula (I);

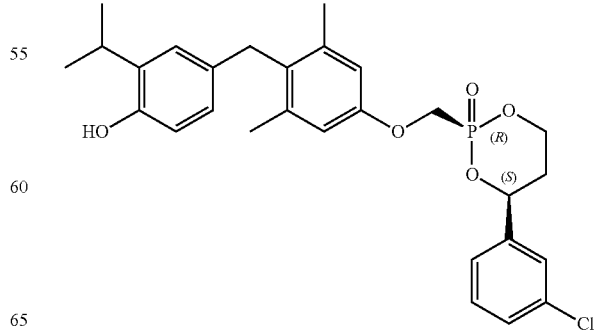

(b) 16 to 600 parts of a meltable and dispersible carrier comprising poloxamer and polyethylene glycol with a poloxamer-to-polyethylene glycol weight ratio in the range of 1:0.5 to 1:27 and (c) 0.2 parts to 100 parts of a non-volatile weak acid.

Another aspect of the present application relates to a method for preparing the pharmaceutical composition of the present application. The method comprises the steps of (1) adding polyethylene glycol, poloxamer and non-volatile weak acid in sequential order of melting point from low to high, at a temperature 5-15° C. higher than the melting point of polyethylene glycol to form a melting matrix; and (2) adding the compound of Formula (I) to the melting matrix to form a molten product.

The preparation process described in the present application improves the solubilization of the compound of Formula (I). The preparation process is simple and easy to implement, without the use of organic solvents, and is carried out at temperatures not exceeding 100° C., so that the stability of the compound of Formula (I) is not affected by the preparation process.

Figure 1:
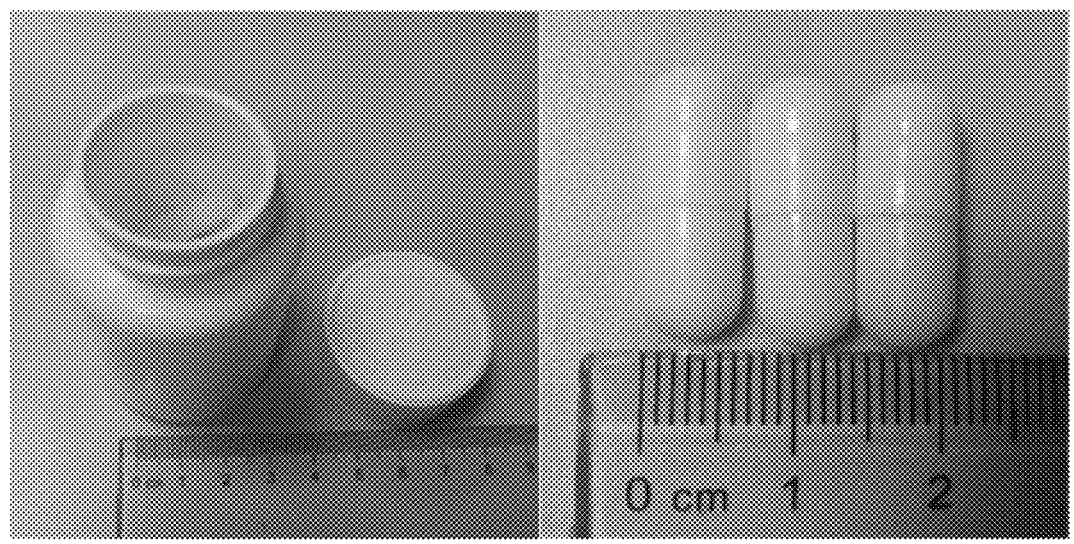
FIG. 1 shows the packaging and appearance of the capsules of the E1 prescription in Example 1.

While the present disclosure will now be described in detail, and it is done so in connection with the illustrative embodiments, it is not limited by the particular embodiments illustrated in the figures and the appended claims.

DETAILED DESCRIPTION OF THE INVENTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

The term "pharmaceutically-acceptable excipient" as used herein refers to one or more compatible solid or liquid filler, diluents or encapsulating substances that are suitable for administration into a human. The term "pharmaceutically acceptable carrier" refers to pharmaceutically-acceptable materials, compositions or vehicles, such as liquid or solid fillers, diluents, excipients, solvents or encapsulating materials, involved in carrying or transporting any subject composition or component thereof from one organ, or portion of the body, to another organ, or portion of the body. The term "carrier" denotes an organic or inorganic ingredient, natural or synthetic, with which the active ingredient is combined to facilitate administration. Each excipient or carrier must be "acceptable" in the sense of being compatible with the subject composition and its components and not injurious to the patient. The components of the pharmaceutical compositions also are capable of being co-mingled with the molecules of the present invention, and with each other, in a manner such that there is no interaction that would substantially impair the desired pharmaceutical efficacy.

The term "effective amount" as used herein refers to the amount of a therapy needed to alleviate at least one or more symptoms of the disease or disorder (e.g., inflammation or renal inflammation), and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

I. Pharmaceutical Composition

One aspect of the present application relates to a pharmaceutical composition which comprises the following components in parts by weight:

(a) 1 part of the compound of Formula (I);

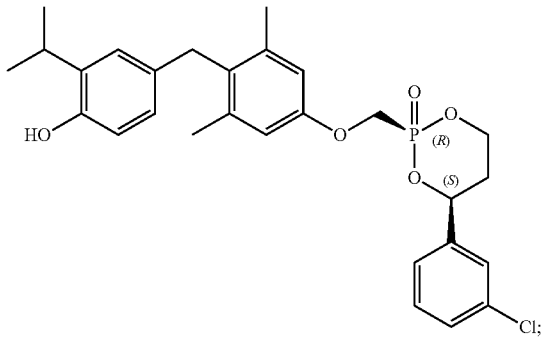

and (b) 1 parts to 1000 parts of meltable and dispersible carrier; wherein the meltable and dispersible carrier comprises poloxamer and polyethylene glycol, wherein the weight ratio of poloxamer and polyethylene glycol is 1:0.1 to 1:100.

In some embodiments, the composition further comprises: c) 0.1 parts to 200 parts of non-volatile weak acid.

In some embodiments, the composition comprises (a) 1 part of the compound of Formula (I); (b) 16 parts to 600 parts of meltable and dispersible carrier; wherein the meltable and dispersible carrier comprises poloxamer and polyethylene glycol, wherein the weight ratio of poloxamer and polyethylene glycol is 1:0.5 to 1:27; and (c) 0.2 parts to 100 parts of non-volatile weak acid.

In some embodiments, the above-described composition comprises 18 parts to 500 parts of meltable and dispersible carrier. In some embodiments, the above-described composition comprises 50 parts to 150 parts of meltable and dispersible carrier. In some embodiments, the above-described composition comprises 98 parts of meltable and dispersible carrier.

In some embodiments, the weight ratio of poloxamer and polyethylene glycol in the above-described composition is in the range of 1:2 to 1:25, 1:2 to 1:20, 1:2 to 1:16, 1:2 to 1:12, 1:2 to 1:8 or 1:2 to 1:6. In some embodiments, the weight ratio of poloxamer and polyethylene glycol in the above-described composition is 1:4.4.

In some embodiments, the above-described composition comprises 0.2-100, 0.3-75, 0.4-50, 0.5-25, 0.6-10, 0.7-5, 0.8-2, 0.9-1.2 parts of non-volatile weak acid. In some embodiments, the above-described composition comprises 1 part of non-volatile weak acid.

In some embodiments, the above-described composition comprises (a) 1 part of the compound of Formula (I); (b) 16 parts to 600 parts of meltable and dispersible carrier; wherein the meltable and dispersible carrier comprises poloxamer and polyethylene glycol, wherein the weight ratio of poloxamer and polyethylene glycol is 1:0.5 to 1:27; and (c) 0.2 parts to 100 parts of non-volatile weak acid.

In some embodiments, the above-described composition comprises (a) 1 part of the compound of Formula (I); (b) 18 parts of poloxamer and 80 parts of polyethylene glycol; and (c) 1 part of non-volatile weak acid.

In some embodiments, the composition is used for the treatment of steatohepatitis.

In some embodiments, the pharmaceutical composition of the present application has a melting temperature is between 35° C. and 65° C. The pharmaceutical composition can exist in a transparent homogeneous phase after being melted. The viscosity of the pharmaceutical composition after melting (during filling) is less than 1500 mPa. S.

In some embodiments, the weight ratio of components (a):(b):(c) in the composition is 1:16-600:0.2-100 (i.e., 1 part by weight of component (a), 16-600 parts by weight of component (b), and 0.2-100 parts by weight of component (c)). In certain embodiments, the weight ratio of components (a):(b):(c) in the composition is in the range of 1:16-700: 0.2-100, 1:16-500:0.2-100, 1:16-400:0.2-100, 1:16-300:0.2-100, 1:16-200:0.2-100, 1:16-150:0.2-100, 1:16-100:0.2-100, 1:18-700:0.2-100, 1:18-600:0.2-100, 1:18-500:0.2-100, 1:18-400:0.2-100, 1:18-300:0.2-100, 1:18-200:0.2-100, 1:18-150:0.2-100, 1:18-100:0.2-100, 1:50-700:0.2-100, 1:50-600:0.2-100, 1:50-500:0.2-100, 1:50-400:0.2-100, 1:50-300:0.2-100, 1:50-200:0.2-100, 1:50-150:0.2-100, 1:50-100:0.2-100, 1:100-700:0.2-100, 1:100-600:0.2-100, 1:100-500:0.2-100, 1:100-400:0.2-100, 1:100-300:0.2-100, 1:100-200:0.2-100, 1:100-150:0.2-100, 1:150-700:0.2-100, 1:150-600:0.2-100, 1:150-500:0.2-100, 1:150-400:0.2-100, 1:150-300:0.2-100, 1:150-200:0.2-100, 1:200-700:0.2-100, 1:200-600:0.2-100, 1:200-500:0.2-100, 1:200-400:0.2-100, 1:200-300:0.2-100, 1:300-700:0.2-100, 1:300-600:0.2-100, 1:300-500:0.2-100, 1:300-400:0.2-100, 1:400-700:0.2-100, 1:400-600:0.2-100, 1:400-500:0.2-100, 1:500-700:0.2-100, 1:500-600:0.2-100 or 1:600-700:0.2-100.

In certain embodiments, the weight ratio of components (a):(b):(c) in the composition is in the range of 1:16-700: 0.3-75, 1:16-500:0.3-75, 1:16-400:0.3-75, 1:16-300:0.3-75, 1:16-200:0.3-75, 1:16-150:0.3-75, 1:16-100:0.3-75, 1:18-700:0.3-75, 1:18-600:0.3-75, 1:18-500:0.3-75, 1:18-400: 0.3-75, 1:18-300:0.3-75, 1:18-200:0.3-75, 1:18-150:0.3-75, 1:18-100:0.3-75, 1:50-700:0.3-75, 1:50-600:0.3-75, 1:50-500:0.3-75, 1:50-400:0.3-75, 1:50-300:0.3-75, 1:50-200: 0.3-75, 1:50-150:0.3-75, 1:50-100:0.3-75, 1:100-700:0.3-75, 1:100-600:0.3-75, 1:100-500:0.3-75, 1:100-400:0.3-75, 1:100-300:0.3-75, 1:100-200:0.3-75, 1:100-150:0.3-75, 1:150-700:0.3-75, 1:150-600:0.3-75, 1:150-500:0.3-75, 1:150-400:0.3-75, 1:150-300:0.3-75, 1:150-200:0.3-75, 1:200-700:0.3-75, 1:200-600:0.3-75, 1:200-500:0.3-75, 1:200-400:0.3-75, 1:200-300:0.3-75, 1:300-700:0.3-75, 1:300-600:0.3-75, 1:300-500:0.3-75, 1:300-400:0.3-75, 1:400-700:0.3-75, 1:400-600:0.3-75, 1:400-500:0.3-75, 1:500-700:0.3-75, 1:500-600:0.3-75 or 1:600-700:0.3-75.

Compound of Formula (I)

The compound of Formula (I) may exist in a crystalline powder or an amorphous form that does not contain a solvent or crystal water. In some embodiments, the compound of formula (I) is in the form of a hydrate or solvate.

b) Meltable and Dispersible Carrier

The meltable and dispersible carrier comprises poloxamer and polyethylene glycol.

In some embodiments, the poloxamer is an α-hydrogen-ω-hydroxy poly(oxyethylene)-poly(oxypropylene)-poly (oxyethylene) block copolymer. In some embodiments, the poloxamer comprises one or more poloxamers selected from the group consisting of poloxamer 407, poloxamer 401, poloxamer 338, poloxamer 331, poloxamer 237, poloxamer 188, poloxamer 181 and poloxamer 108. In some embodiments, the poloxamer is poloxamer 188 with a polyoxypropylene unit number of 75-85, and an average molecular weight of 7,680-9,510 dalton.

In some embodiments, the polyethylene glycol comprises one or more of polyethylene glycol with an average molecular weight between 200 and 20000. Examples of such polyethylene glycols include, but are not limited to, polyethylene glycols 300, polyethylene glycol 400, polyethylene glycol 600, polyethylene glycol 1000, polyethylene glycol 1500, polyethylene glycol 3350, polyethylene glycol 4000, polyethylene glycol 6000, polyethylene glycol 8000, polyethylene glycol 10000 and polyethylene glycol 20000.

In some embodiments, the polyethylene glycol comprises one or more polyethylene glycols selected from the group consisting of polyethylene glycol 1000, polyethylene glycol 1500, polyethylene glycol 3350, polyethylene glycol 4000, polyethylene glycol 6000, polyethylene glycol 8000 or polyethylene glycol 10000.

In some embodiments, the pharmaceutical composition comprises, in parts by weight, 18 to 500 parts of a meltable and dispersible carrier.

In some embodiments, the pharmaceutical composition comprises, in parts by weight, 18-400, 18-350; 18-300; 18-250, 18-200, 18-150, 18-100, 50-500; 50-400; 50-350, 50-300, 50-250, 50-200, 50-150, 150-500, 150-400, 150-300, 150-200, 200-500, 200-400, 200-300, 300-500, 300-400 or 400-500 parts of a meltable and dispersible carrier.

In some embodiments, in the meltable and dispersible carrier, the weight ratio of poloxamer and polyethylene glycol is in the range of 1:2 to 1:25.

In some embodiments, the weight ratio of poloxamer and polyethylene glycol is in the range of 1:2 to 1:20, 1:2 to 1:15, 1:2 to 1:10, 1:2 to 1:8, 1:2 to 1:6, 1:3 to 1:25, 1:3 to 1:20, 1:3 to 1:15, 1:3 to 1:10, 1:3 to 1:8, 1:3 to 1:6, 1:5 to 1:25, 1:5 to 1:20, 1:5 to 1:15, 1:5 to 1:10, 1:5 to 1:8, 1:10 to 1:25, 1:10 to 1:20, 1:10 to 1:15, 1:15 to 1:25, 1:15 to 1:20 or 1:20 to 1:25.

c) Non-Volatile Weak Acid

The non-volatile weak acid can be any non-volatile weak acid or mixtures thereof. Examples of non-volatile weak acid include, but are not limited to, malic acid, maleic acid, niacin, tartaric acid, phosphoric acid, citric acid monohydrate, anhydrous citric acid, vitamin C and acidic amino acids. In some embodiments, the non-volatile weak acid is anhydrous citric acid, citric acid monohydrate or a mixture thereof.

In some embodiments, the pharmaceutical composition contains 0.3-75, 0.3-50, 0.3-25, 0.3-15, 0.3-5, 0.3-2, 0.3-1.5, 0.5-75, 0.5-50, 0.5-25, 0.5-15, 0.5-5, 0.5-2, 0.5-1.5, 0.7-75, 0.7-50, 0.7-25, 0.7-15, 0.7-5, 0.7-2, 0.7-1.5, 0.7-1.2, 1-5, 5-25, 5-50, 5-75, 25-50, 25-75 or 50-75 parts by weight non-volatile weak acid.

d) Other Components

In some embodiments, the pharmaceutical composition of the present application can also contain other compatible components, including but not limited to, one or more of: cetyl alcohol, cetostearyl alcohol, stearyl alcohol, oleic acid, stearin acid, medium chain glycerin triester, glyceryl dipalmitate stearate, propylene glycol monocaprylate, glyceryl behenate (sold under the trademark COMPRITOL® 888 ATO), polyoxyethylene-8 glyceryl behenate (sold under the trademark COMPRITOL® 5 ATO), single and double hard fatty acid glycerides, soybean oil mixed fatty acid glycerides, polyethylene glycol-32 stearate (sold under the trademark GELUCIRE® 48/16), lauroyl polyoxyethylene-32 glyceride (sold under the trademark GELUCIRE® 44/14), stearoyl Polyoxyethylene glyceride (sold under the trademark GELUCIRE® 50/13), propylene glycol dicaprylic acid caprate, oleoyl polyoxyethylene glyceride, caprylic acid capric acid polyethylene glycol glyceride, propylene glycol monolaurate, glyceryl monolinoleate, glyceryl monooleate, polyglyceryl oleate, glyceryl distearate, diethylene glycol monoethyl ether, polyethylene glycol 15-hydroxy stearate (sold under the trademark KOLLIPHORe® HS15), polyoxyethylene (35), castor oil (sold under the trademark KOLLIPHOR® polyoxyethylene 40 hydrogenated castor oil (sold under the trademark KOLLIPHOR® RH40), vitamin E and hydrogenated castor oil.

II. Methods of Preparation

Another aspect of the present application relates to a method for preparing the pharmaceutical composition of the present application. In some embodiments, the preparation method of the pharmaceutical composition of the present application includes the following steps:

(1) Adding polyethylene glycol, poloxamer and non-volatile weak acid in sequential order of melting point from low to high under the condition of 5-15° C. higher than the melting temperature of polyethylene glycol to form a melting matrix;

(2) Adding the compound of Formula (I) to the melting matrix to melt the compound and form a molten product.

In some embodiments, a debubbling step is further included between the steps (1) and (2). In some embodiments, the debubbling step is performed by settling (i.e., letting the melting matrix of step (1) sit still in the container for a period of time (for 10-60 minutes), by sonication or by vacuum degassing (i.e., applying a negative pressure to the melting matrix) the melting mixture of step (1), while maintaining the same temperature.

In some embodiments, the above preparation method further includes the step of filling the molten product obtained in step (2) into capsules. In a particular embodiment, the step of filling the capsules is carried out at a temperature of 55° C.±5° C. for no more than 4 hours.

In other embodiments, the preparation method of the pharmaceutical composition of the present application includes the following steps:

(1) Preparation of a melting matrix: at 5-15° C. higher than the melting temperature of the carrier (such as polyethylene glycol), in the sequential order of melting point from low to high, add carrier excipients (such as polyethylene glycol and poloxamer) and pH adjuster (non-volatile weak acid) to form a melting matrix;

(2) debubbling: remove bubbles in the melting matrix by settling, sonication, or vacuum degassing;

(3) Addition of the active pharmaceutical ingredient (API): add the compound of Formula (I) to the melting matrix with stirring and continue stirring until the compound is completely melt into the melting matrix to form a molten product;

(4) Fill the capsule: transfer the prepared molten product to the preheated heat preservation barrel of the capsule filling machine, turn on the stirring function; and use the preset filling parameters to fill the molten product into hard gelatin capsules (control the difference of average filling amount ≤2.5%, the single capsule filling volume difference ≤5.0%), cover the capsule, and seal (optionally, choose not to seal);

(5) Cooling: quickly cool and solidify the contents in the capsules by passing the capsules on a pack conveyor belt with compressed air or spreading the capsules on a flat surface at room temperature;

(6) Packaging: Pack the capsules in moisture-proof packaging, such as high-density ethylene bottles or composite aluminum film packaging.

The capsules prepared by this method need to be sealed and stored in a cool place below room temperature (not exceeding 15° C.), preferably at 2-8° C.

III. Methods of Treatment

Another aspect of the present application relates to a method for treating steatohepatitis, including non-alcoholic steatohepatitis (NASH) or a steatohepatitis related condition in a subject. The method comprises the step of administering to a subject in need of such treatment, an effective amount of the pharmaceutical composition of the present application. In some embodiments, the pharmaceutical composition of the present application is administered in a capsule form. In some embodiments, the pharmaceutical composition of the present application is administered twice a day, daily or every other day.

Examples of steatohepatitis related conditions include, but are not limited to, fibrosis, ascites and esophageal varices.

In certain embodiments, the pharmaceutical composition is an oral preparation, preferably a capsule, more preferably a gelatin capsule or a hydroxypropyl methylcellulose capsule.

In certain embodiments, the total amount of the pharmaceutical composition (content) in the capsule can be between 100 mg and 650 mg, and the content can be poured into a gelatin capsule or a hydroxypropyl methylcellulose capsule. In certain embodiments, according to the quality of the contents, pour the content into the appropriate type of capsule shell. In certain embodiments, the available capsule types include No. 5 capsule, No. 4 capsule, No. 3 capsule, No. 2 capsule, No. 1 capsule and No. 0 capsule.

Another aspect of the present application relates to the use of the pharmaceutical composition, or the pharmaceutical composition prepared according to the preparation method herein, in the preparation of a medicament for treating steatohepatitis.

This application discloses that unexpectedly by designing the compound represented by Formula (I) into a semi-solid capsule with a specific prescription ratio, this helps to greatly improve the in vitro dissolution rate of the compound represented by Formula (I). At the same time, due to the mild preparation conditions, this formulation herein can ensure the stability of the compound represented by Formula (I).

The advantages of the subject matter of the present application are:

(1) The use of the pharmaceutical composition of the present application can greatly improve the dissolution rate of the compound represented by Formula (I), and can achieve the goal of solubilizing at concentrations more than 10,000 times the measured solubility of the compound so that an effective amount of therapeutic drug can be delivered;

(2) Due to the use of the pharmaceutical composition of the present application, the pharmaceutical preparation of the compound represented by Formula (I) can be prepared at a relatively mild temperature (<65° C.), avoiding the occurrence of drug degradation reactions under high-temperature processes;

(3) The preparation process of the pharmaceutical composition of the present application is simple, the core process is melting, which is suitable for industrial production, and can effectively avoid defects such as dust pollution in the granulation process, explosion-proof and organic solvent residual problems in the spray drying solid dispersion process, and heat problems, such as high temperature degradation during melt extrusion.

The present application is further illustrated by the following examples that should not be construed as limiting. The contents of all references, patents, and published patent applications cited throughout this application, as well as the Figures and Tables, are incorporated herein by reference.

EXAMPLES

Example 1

Formulation Composition:

| Composition prescription | A1 | B1 | C1 | D1 | E1 | F1 | G1 |
|---|---|---|---|---|---|---|---|
| Compound of Formula (I) (mg) | 1 | 1 | 2.5 | 5 | 5 | 7.5 | 10 |
| Polyethylene glycol 400 (mg) | 70 | 0 | 0 | 0 | 0 | 0 | 0 |
| Polyethylene glycol 1000 (mg) | 126 | 0 | 150 | 35 | 300 | 250 | 300 |
| Polyethylene glycol 4000 (mg) | 0 | 378 | 0 | 5 | 0 | 0 | 0 |
| Polyethylene glycol 6000 (mg) | 208 | 100 | 100 | 20 | 100 | 62 | 185 |
| Poloxamer 188 (mg) | 20 | 20 | 40 | 30 | 90 | 28 | 150 |
| Anhydrous citric acid (mg) | 75 | 1 | 7.5 | 5 | 5 | 2.5 | 5 |
| Content weight (mg) | 500 | 500 | 300 | 100 | 500 | 350 | 650 |
| Proportion of the compound of Formula (I) the (wt %) | 0.2 | 0.2 | 0.8 | 5.0 | 1.0 | 2.1 | 1.5 |
| Proportion of Poloxamer 188 (wt %) | 4.0 | 4.0 | 13.3 | 30.0 | 18.0 | 8.0 | 23.1 |
| Polyethylene glycol percentage (wt %) | 80.8 | 95.6 | 83.3 | 60.0 | 80.0 | 89.1 | 74.6 |
| Proportion of anhydrous citric acid (wt %) | 15.0 | 0.2 | 2.5 | 5.0 | 1.0 | 0.7 | 0.8 |
| Type of gelatin capsule filled | No. 1 | No. 1 | No. 3 | No. 5 | No. 1 | No. 2 | No. 0 |

Preparation Process:

1. Preparation of melting matrix: add polyethylene glycol, poloxamer 188 and anhydrous citric acid in sequential order of melting point at 5-15° C. higher than the melting temperature of the carrier to form a melting matrix;

2. Removal of bubbles: remove bubbles in the melting matrix by settling, sonication, or vacuum degassing;

3. Addition of the API: add the compound of Formula (I) under stirring, and continue stirring to completely melt the compound in the matrix to form a molten product;

4. Capsule filling: transfer the prepared molten product to the preheated insulation barrel of the capsule filling machine, turn on the stirring function, pour the molten product into hard gelatin capsules with preset filling parameters (control average loading difference ≤2.5%, single capsule packing difference ≤5.0%), and close the capsule cap;

5. Cooling: cool and solidify the contents of the capsules by placing the capsules on a conveyor belt with compressed air or spreading the capsules on a flat surface at room temperature;

6. Packaging: put the capsule into a high-density ethylene bottle and seal it with aluminum film;

7. Storage: store the packaged bottled compound capsules of Formula (I) at 2-8° C.

Comparative Example 1

Formulation Composition:

TABLE 2

| Formulation composition of Comparative Example 1 | | | | | |
|---|---|---|---|---|---|
| Formulation Composition | a1 | b1 | c1 | d1 | e1 |
| Compound of Formula (I) (mg) | 5 | 5 | 5 | 5 | 5 |
| Polyethylene glycol 1000 (mg) | 495 | 0 | 0 | 0 | 240 |
| Polyethylene glycol 6000 (mg) | 0 | 495 | 0 | 0 | 240 |
| Poloxamer 188 (mg) | 0 | 0 | 495 | 0 | 0 |
| Anhydrous citric acid (mg) | 0 | 0 | 0 | 195 | 15 |
| Content weight (mg) | 500 | 500 | 500 | 200 | 500 |
| Proportion of compound of Formula (I) (wt %) | 1.0 | 1.0 | 1.0 | 2.5 | 1.0 |
| Proportion of Poloxamer 188 (wt %) | 0.0 | 0.0 | 99.0 | 0.0 | 0.0 |
| Polyethylene glycol percentage (wt %) | 99.0 | 99.0 | 0.0 | 0.0 | 96.0 |
| Proportion of anhydrous citric acid (wt %) | 0.0 | 0.0 | 0.0 | 97.5 | 3.0 |
| Type of gelatin capsule filled | No. 1 | No. 1 | No. 1 | No. 1 | No. 1 |

Preparation Process:

Formulations a1, b1, c1 and e1:

1. Preparation of melting matrix: under the condition of 5-15° C. higher than the melting temperature of the carrier, the components other than the compound represented by Formula (I) are melted in sequential order of melting point from low to high to form a melting matrix;

2. Removal of bubbles: remove bubbles in the melting matrix by settling, sonication, or vacuum degassing;

3. Addition of the API: add the compound of Formula (I) with stirring, and continue stirring to completely melt the compound in the matrix;

4. Capsule filling: transfer the prepared molten content to the preheated insulation barrel of the capsule filling machine, turn on the stirring function, and pour the molten content into hard gelatin capsules with preset filling parameters (control average loading difference ≤2.5%, single loading difference ≤5.0%), cover the capsule cap;

5. Cooling: cool and solidify the contents of the capsules by placing the capsules on a conveyor belt with compressed air or spreading the capsules on a flat surface at room temperature;

6. Packaging: Put the capsule into a high-density vinyl bottle and seal it with aluminum film;

7. Storage: Store the packaged bottled compound capsules of Formula (I) at 2-8° C.

Formulation d1:

1. Pass the compound of Formula (I) and the crushed anhydrous citric acid through 40 mesh and 60 mesh sieves, respectively;

2. Mixing: Mix the compound of Formula (I) and anhydrous citric acid powder;

3. Capsule filling: 200 mg/capsule, manually filled into No. 1 capsule on the capsule plate;

4. Packaging: Put the capsule into a high-density vinyl bottle and seal it with aluminum film;

5. Storage: Store the packaged bottled compound capsules of Formula (I) at 2-8° C.

Comparative Example 2

Composition of formulation:

TABLE 3

| Formulation composition of Comparative Example 2 | | | | |
|---|---|---|---|---|
| Composition formulation | a2 | b2 | c2 | d2 |
| Compound represented by Formula (1) (mg) | 30 | 5 | 5 | 5 |
| Polyethylene glycol 1000 (mg) | 200 | 75 | 215 | 300 |
| Polyethylene glycol 6000 (mg) | 180 | 50 | 215 | 100 |
| Poloxamer 188 (mg) | 80 | 350 | 15 | 94.5 |
| Anhydrous citric acid (mg) | 10 | 20 | 50 | 0.5 |
| Content weight (mg) | 500 | 500 | 500 | 500 |
| Proportion of compound represented by Formula (I) (wt %) | 6.0 | 1.0 | 1.0 | 1.0 |
| Proportion of Poloxamer 188 (wt %) | 16.0 | 70.0 | 3.0 | 18.9 |
| Polyethylene glycol percentage (wt %) | 76.0 | 25.0 | 86.0 | 80.0 |
| Proportion of anhydrous citric acid (wt %) | 2.0 | 4.0 | 10.0 | 0.1 |
| Type of gelatin capsule filled | No. 1 | No. 1 | No. 1 | No. 1 |

Preparation Process:

1. Preparation of melting matrix: Add polyethylene glycol, poloxamer 188 and anhydrous citric acid in order of melting point at 5-15° C. higher than the melting temperature of the carrier to form a melting matrix;

2. Removal of bubbles: remove bubbles in the melting matrix by settling;

3. Addition of the API: add the compound of Formula (I) under stirring, and continue stirring to completely melt the compound in the melting matrix to form a molten product;

4. Capsule filling: transfer the prepared molten product to the preheated insulation barrel of the capsule filling machine, turn on the stirring function, and pour the molten product into hard gelatin capsules with preset filling parameters (control average loading difference ≤2.5%, single capsule packing difference ≤5.0%), cover the capsule cap;

5. Cooling: cool and solidify the contents of the capsules by placing the capsules on a conveyor belt with compressed air or spreading the capsules on a flat surface at room temperature;

6. Packaging: Put the capsule into a high-density ethylene bottle and seal it with aluminum film;

7. Storage: Store the packaged bottled compound capsules of Formula (I) at 2-8° C.

Effect Example 1

Take the E1 prescription under Example 1 and conduct a pilot and scale-up study on this production technology in a Z4 liquid capsule machine (Shandong Xinma Pharmaceutical Equipment Co., Ltd., SHANDONG SMA PHARMATECH Co., Ltd). The trial production scale is 10,000 capsules/batch. Set the temperature of the mixing tank to 55° C., the temperature of the heating block to 52° C., and the liquid stirring speed to 30.0 rpm.

In the early stage (1000th to 3000th capsule), mid-stage (4000-6000 capsules) and late stage (7000-9000 capsules) of filling, 10 capsules were randomly sampled continuously, and the total capsule weight and the weight of each capsule were weighed. After deducting the blank capsule shell, the average filling volume and the filling volume standard deviation are calculated. The loading differences under different production conditions shown in Table 4, and the appearance of the final product is shown in FIG. 1.

TABLE 4

Filling speed, average weight and deviation at different stages of compound capsules shown in formula (I)

| Filling Time period | Capsule weight (average volume ± standard deviation, Mean ± SD, n = 10) | | | |
|---|---|---|---|---|
| | 1 w grains/ hour | 2 w grains/ hour | 3 w grains/ hour | 4 w grains/ hour |
| Early stage | 577.5 mg ± 1.9 mg | 577.6 mg ± 3.1 mg | 578.1 mg ± 2.5 mg | 577.4 mg ± 4.6 mg |
| Mid-term | 577.8 mg ± 2.1 mg | 577.8 mg ± 2.4 mg | 578.1 mg ± 2.6 mg | 577.6 mg ± 4.5 mg |
| Late | 577.5 mg ± 2.1 mg | 577.9 mg ± 2.8 mg | 578.0 mg ± 3.1 mg | 577.8 mg ± 5.2 mg |
| Yield | 9255 capsules (92.6%) | 9270 Capsules (92.7%) | 9233 Capsules (92.3%) | 9189 Capsules (91.9%) |

Samples were taken from the materials in the mixing barrel at different filling temperatures (50° C., 55° C. and 60° C.) and time (0 h, 1 h, 2 h, 4 h), and related substances were determined. The effects of temperature and heating time on the stability of the samples were investigated. The results are shown in Table 5.

Determination of related substances: octadecyl silane bonded silica gel was used as filler (ACE UltraCore2.5 SuperC18 (4.6*150 mm) or chromatographic column with equivalent performance); use 10 mM potassium dihydrogen phosphate aqueous solution as mobile phase A, use acetonitrile For mobile phase B, perform gradient (volume ratio) elution according to the following table; flow rate: 1.0 ml/min, detection wavelength: 230 nm, column temperature: 45° C.

TABLE 5

| Time (min) | Mobile phase A (%) | Mobile phase B (%) |
|---|---|---|
| 0.00 | 80 | 20 |
| 0.50 | 80 | 20 |
| 8.00 | 45 | 55 |
| 15.00 | 45 | 55 |
| 25.00 | 30 | 70 |
| 50.00 | 15 | 85 |
| 50.10 | 80 | 20 |
| 55.00 | 80 | 20 |

Take an appropriate amount of the compound of Formula (I) and the impurity reference substance, add acetonitrile to dissolve and dilute to prepare a solution containing 0.5 mg of the compound of Formula (I) and 0.001 mg of impurities in each 1 ml, as a system suitability test solution. Precisely measure 10 μl into the liquid chromatograph and record the chromatogram. The separation degree between impurities and adjacent peaks should not be less than 1.5. Take 10 capsules of this product, accurately weigh it, pour the contents into a 100 ml measuring bottle, wash the inner wall of the capsule with acetonitrile in batches, adding the washing liquid into the measuring bottle, add acetonitrile to dissolve and to prepare a formulation containing 0.5 mg per 1 ml of the compound of Formula (I) as the test solution. Accurately measure 10 μl of the test solution, inject it into the liquid chromatograph, and record the chromatogram. Calculate the total amount of impurities and all impurities in the compound capsule of Formula (I) according to the peak area normalization method.

Results:

(1) Under 4 different filling speeds, the filling accuracy of the composition and process (The average filling volume-theoretical filling volume/theoretical filling volume) is less than 1.0%, the precision (standard deviation/average filling volume) is less than 1.0%, and rates for product to pass QC are all over 90%.

(2) At 55° C.±5° C., when the materials were stored in the mixing barrel for 4 hours, the total impurities of related substances increased less than 0.2%. No obvious new single impurity is found.

TABLE 6

Effects of different filling temperatures and filling times on related substances of compounds of formula (I)

| Filling time | Related substances (total impurities, %) | | |
|---|---|---|---|
| | 50° C. | 55° C. | 60° C. |
| 0 h | 1.345 | 1.393 | 1.382 |
| 1 h | 1.452 | 1.395 | 1.482 |
| 2 h | 1.542 | 1.376 | 1.472 |
| 3 h | 1.592 | 1.437 | 1.469 |
| 4 h | 1.492 | 1.451 | 1.483 |
| 4 h increase | 0.147 | 0.058 | 0.101 |

Conclusion: The preparation process of the compound capsule of Formula (I) is simple, and the yield of 10,000/batch is greater than 90%; after filling, the capsule can be quickly solidified at room temperature (within 5 minutes), and there was no leakage between the shell and shell cap (see FIG. 1); this process is prepared at a temperature of 55° C.±5° C., and the total impurities of related substances increase by less than 0.2% after 4 hours of filling, which can effectively avoid drug degradation under high temperature processes.

Effect Example 2

Dissolution profile determination. Take capsules of groups A1-G1 of Example 1 and the capsules of groups a1-e1 of Comparative Example 1, and the capsules under the group a2-d2 under the item of the Comparative Example 2 and put them into the sedimentation basket, at 37° C.±0.5° C., 900 mL of degassed water, 50 rpm paddle method, samples were taken at 10, 20, 30, 45, 60, 90 and 120 min respectively, and the subsequent filtrate was taken and diluted with an equal proportion of methanol to determine the compound of Formula (I) by HPLC Calculate the cumulative dissolution percentage of the compound of Formula (I) in the capsule at different time points.

HPLC determination conditions: select octadecyl silane-bonded silica gel as the filler (Welch Ultimate®XB-C18 4.6*150 mm, 5 μm, or equivalent chromatographic column), with 0.05% trifluoroacetic acid aqueous solution-acetonitrile (30:70) is the mobile phase, the flow rate is 1.0 ml/min, the column temperature is 30° C., and the detection wavelength is 230 nm. Accurately measure 20 μl each of the reference solution and the test solution, and inject them into the liquid chromatograph respectively, record the chromatogram, and calculate the dissolution amount of each particle by the peak area according to the external standard method.

Figure 2:
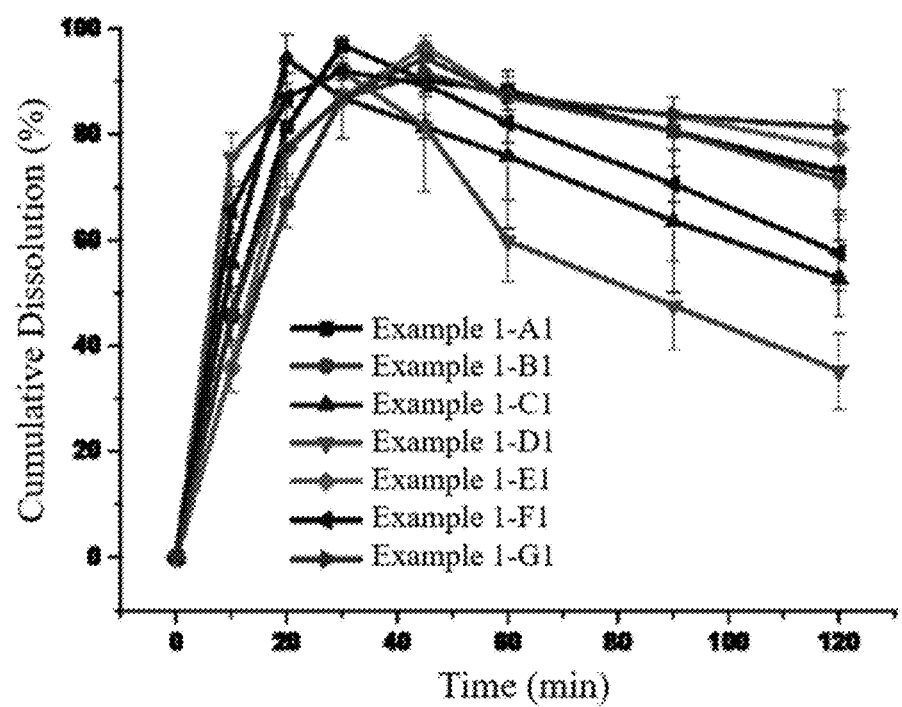
FIG. 2 is a schematic diagram of the dissolution profile in water of the capsules prepared according to the recipes A1 to G1 in Example 1 (n=6)
Figure 3:
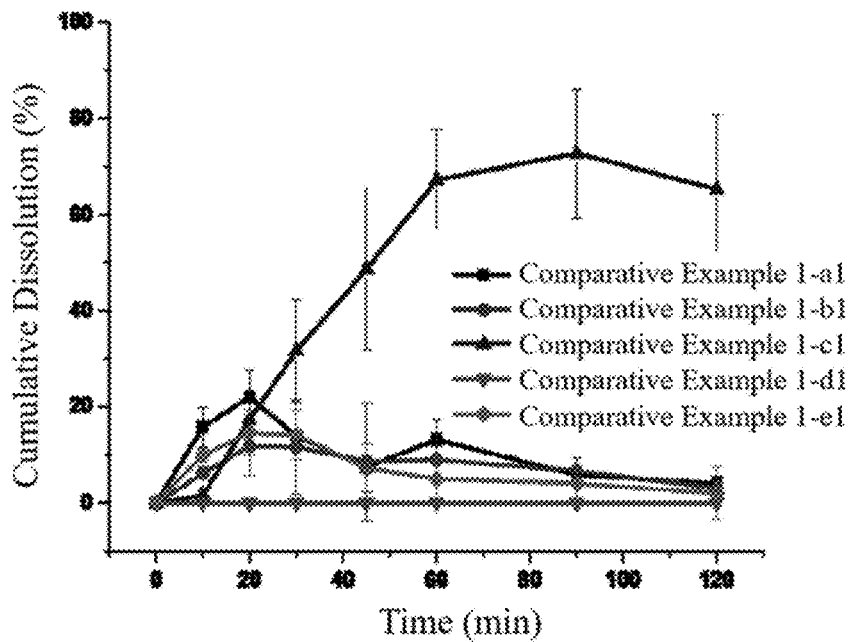
FIG. 3 is the dissolution curve in water of the capsules prepared according to the recipes a1 to e1 in Comparative Example 1 (n=6)
Figure 4:
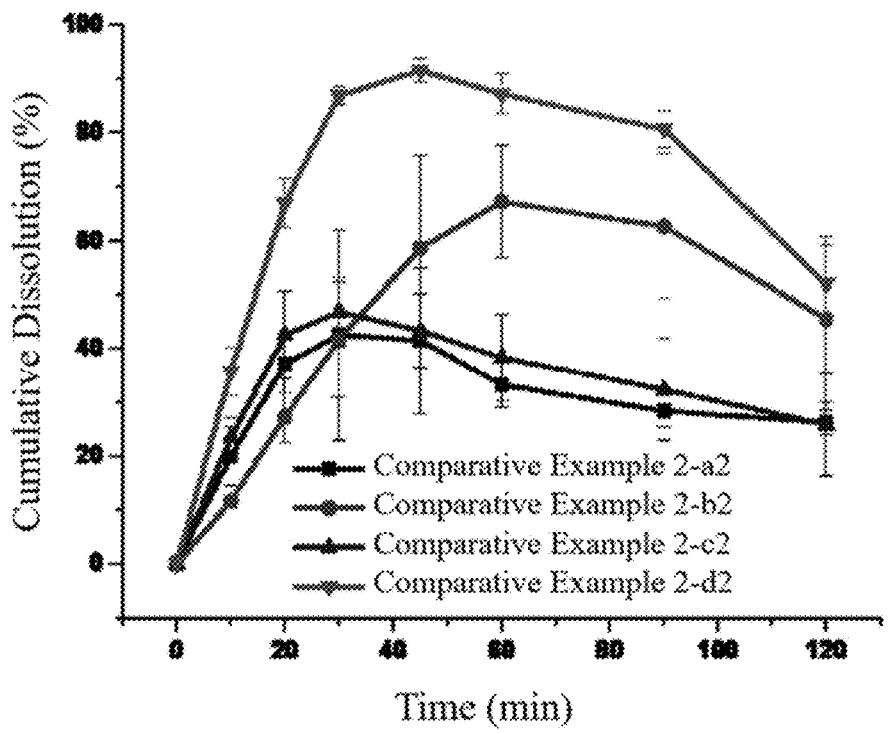
FIG. 4 shows the dissolution curve in water of the capsules prepared according to the recipes a2 to d2 in Comparative Example 2 (n=6).

Results:

(1) As shown in FIG. 2, under the formulation and ratio obtained by the screening (Example 1), the compound of Formula (I) can achieve the result of dissolution of >85% between 20-40 minutes, and can maintain a longer super-saturation time (2) The compound of Formula (I) can be quickly melted in a single polyethylene glycol 1000, polyethylene glycol 6000 or poloxamer 188, and cooled and solidified to obtain a uniform semi-solid. As shown in FIG. 3, when the three auxiliary materials in Comparative Example 1 are used alone, the highest point dissolution in water is only 22.0%, 11.8%, and 67.3%, respectively. Anhydrous citric acid has no solubilizing effect on the compound of Formula (I), and the dissolution within 2 hours is less than 0.5%. In the formulation e1 without poloxamer 188, the highest dissolution rate of the compound of Formula (I) was only 14.5%.

(3) In Comparative Example 2, in the formula a2, the Formula (I) formula ratio of the compound of the Formula (I) is 6% (greater than the upper limit of the optimized ratio 5%), although polyethylene glycol, poloxamer 188 and anhydrous citric acid Within the ratio range, but the maximum dissolution rate of the prescription in 20 minutes is less than 50%. In prescriptions b2 and c2, the dosage of poloxamer 188 exceeded the upper and lower limits of the optimized range respectively, and the highest dissolution rates of the obtained capsules were all less than 70%.

Conclusion: In the formulation with polyethylene glycol as the carrier alone, although the compound of Formula (I) can melt and disperse in it to form a solid dispersion, the overall dissolution effect is not good, the highest value is less than 25%; Poloxamer 188. Although poloxamer 188 alone can increase the dissolution of the compound of formula (I), better solubilization effect can be achieved when used in combination with polyethylene glycol. Therefore, for the capsule of compound of formula (I), satisfactory solubilization effect can be obtained only when the components are kept in a reasonable proportion and used together.

Effect Example 3

Stability investigation: Take 30 capsules of E1 under Example 1 and d2 under Comparative Example 2 and place them in a high-density polyethylene bottle. After sealing with aluminum film, keep them at 5° C.±3° C. for a long time. The samples were inspected for 3 months, and samples were taken at preset time points to determine related substances.

Related substance determination method: The related substance determination method under the same effect as Example 1.

Results: As shown in Table 6, after it was made into capsules, the Formulation E1 of Example 1 (with 1.0% anhydrous Citric acid) can significantly inhibit and reduce the formation and growth of impurity Z3, while d2 prescription group in comparative example 2 (with 0.1% anhydrous citric acid) can not inhibit and reduce the formation and growth of impurity Z3, and both single impurity Z3 and total impurity tend to increase in the process of stable sample retention.

TABLE 7

Effect of Citric Acid Percentage on Related Substances to Compounds of Formula (I)

| | Related substances (%) | | | | | | | | |
|---|---|---|---|---|---|---|---|---|---|
| | E1 Prescription Capsule of Example 1 | | | | | | | D2 of Comparative Example 2 | |
| | 200 Small test batches | | 10,000-capsule Pilot batches (R4119004) | | 10,000-capsule Pilot batches (R4119005) | | 10,000-capsule Pilot batches (R4119006) | | Prescription capsule 200 Small test batches |
| Storage time | Total Impurities | Impurity Z3 rrt = 1.14) | Total Impurities | Impurity Z3 rrt = 1.14) | Total Impurities | Impurity Z3 rrt = 1.14) | Total Impurities | Impurity Z3 rrt = 1.14) | Total Impurities | Impurity Z3 rrt = 1.14) |
| API | 1.05 | 0.13 | 2.40 | 1.50 | 2.40 | 1.50 | 2.40 | 1.50 | 1.05 | 0.13 |
| 0 Month | 1.15 | 0.09 | 1.70 | 1.10 | 1.70 | 1.10 | 1.70 | 1.10 | 1.20 | 0.18 |
| 1 month | 0.98 | 0.04 | / | / | / | / | / | / | 1.22 | 0.20 |
| 1.5 Month | / | / | 1.00 | 0.38 | 1.00 | 0.40 | 1.20 | 0.56 | / | / |
| 3 month | 1.05 | 0.02 | 0.80 | 0.17 | 0.78 | 0.19 | 0.86 | 0.18 | 1.37 | 0.23 |
| 6 Month | / | / | 0.69 | 0.028 | 0.69 | 0.036 | 0.69 | 0.037 | / | / |
| 9 Month | / | / | 0.71 | Not detected | 0.67 | Not detected | 0.70 | Not detected | / | / |
| 12 Month | / | / | 0.80 | Not detected | 0.76 | Not detected | 0.80 | Not detected | / | / |

Conclusion: Adding and keep a certain concentration of inorganic weak acid in the formulation of current invention can inhibit and reduce the increase of impurity Z3 during the preparation process and long-term storage, which is very important to ensure the stability of the preparation.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A pharmaceutical composition, comprising the following components in parts by weight:
   (a) 1 part of a compound of Formula I

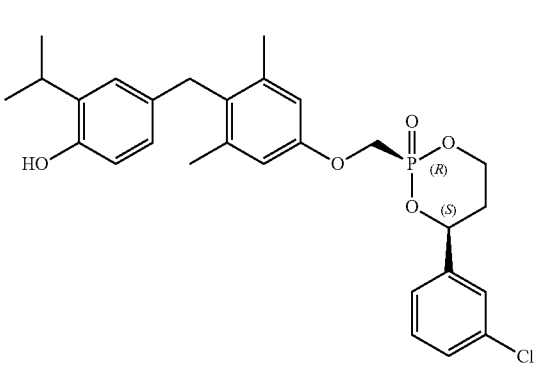

(b) 16 to 600 parts of a meltable and dispersible carrier comprising poloxamer and polyethylene glycol with a poloxamer-to-polyethylene glycol weight ratio in the range of 1:0.5 to 1:27; and
   (c) 0.2 parts to 100 parts of a non-volatile weak acid.

2. The pharmaceutical composition of claim 1, comprising 18 to 500 parts of meltable and dispersible carrier.

3. The pharmaceutical composition of claim 2, wherein the meltable and dispersible carrier comprises poloxamer and polyethylene glycol at a poloxamer-to-polyethylene glycol weight ratio in the range of is 1:2 to 1:25.

4. The pharmaceutical composition of claim 1, wherein the pharmaceutical composition comprises from 0.3 to 75 parts of a non-volatile weak acid.

5. The pharmaceutical composition of claim 1, wherein the compound of Formula (I) is present as a crystalline powder, in an amorphous form containing no solvent or crystal water, or as a hydrate or solvate.

6. The pharmaceutical composition of claim 1, wherein the poloxamer has a number average molecular weight in the range from 7,680 dalton to 9,510 dalton.

7. The pharmaceutical composition of claim 1, wherein the non-volatile weak acid is selected from the group consisting of malic acid, maleic acid, niacin, tartaric acid, phosphoric acid, citric acid monohydrate, anhydrous citric acid, vitamin C, acidic amino acids and mixtures thereof.

8. The pharmaceutical composition of claim 1, wherein the non-volatile weak acid is anhydrous citric acid, citric acid monohydrate, or a mixture thereof.

9. The pharmaceutical composition of claim 1, wherein the polyethylene glycol has a number average molecular weight in the range from 200 dalton to 20,000 dalton.

10. The pharmaceutical composition of claim 1, wherein the polyethylene glycol has a number average molecular weight in the range from 1,000 dalton to 10,000 dalton.

11. The pharmaceutical composition of claim 1, wherein the pharmaceutical composition further comprises one or more additional components selected from the group consisting of cetyl alcohol, cetostearyl alcohol, stearyl alcohol, oleic acid, stearic acid, medium chain triglycerides, dipalmitate glyceride, propylene glycol monocaprylate, glyceryl behenate, glyceryl monostearate, propylene glycol monolaurate, glyceryl monolinoleate, glyceryl monooleate, polyglyceryl oleate, glyceryl distearate, diethylene glycol monoethyl ether, vitamin E, and hydrogenated castor oil.

12. The pharmaceutical composition of claim 1, wherein the pharmaceutical composition is sealed in a capsule.

13. The pharmaceutical composition of claim 12, wherein the capsule is a gelatin capsule or a hydroxypropyl methylcellulose capsule.

14. The pharmaceutical composition of claim 1, wherein the composition has a melting temperature of 35-65° C. and an after melting viscosity of less than 1500 mPa·S.

15. The pharmaceutical composition of claim 14, comprising:
   1 part of the compound of Formula (I); 18 parts of poloxamer, 80 parts of polyethylene glycol, and 1 part of a non-volatile weak acid.

16. A method for preparing the pharmaceutical composition of claim 1, which comprises the following steps:
   (1) adding polyethylene glycol, poloxamer and non-volatile weak acid in sequential order of melting point from low to high, at a temperature 5-15° C. higher than the melting point of polyethylene glycol to form a melting matrix; and
   (2) adding the compound of Formula (I) to the melting matrix to form a molten product.

17. The method of claim 16, further comprising the step of:
   debubbling the melting matrix before the addition of the compound of Formula (I).

18. The preparation method of claim 16, further comprises a step of:
   filling capsules with the molten product, wherein filling is carried out at a temperature in the range of 55° C.±5° C. and the filling time is no more than 4 hours.

19. A method for treating steatohepatitis in a subject in need thereof, the method comprising a step of administering to the subject an effective amount of the pharmaceutical composition of claim 1.

* * * * *